United States Patent [19]

Johnson et al.

[11] Patent Number: 5,364,594
[45] Date of Patent: Nov. 15, 1994

[54] METHOD AND APPARATUS FOR THE COULOMETRIC DETECTION OF DISSOLVED GASES PARTICULARLY $TCO_2$ IN SEAWATER

[75] Inventors: Kenneth M. Johnson, Wading River, N.Y.; John M. Sieburth, West Kingston, R.I.

[73] Assignee: The Board of Governors for Higher Education, State of Rhode Island and Providence Plantations, Providence, R.I.

[21] Appl. No.: 71,525

[22] Filed: Jun. 3, 1993

Related U.S. Application Data

[63] Continuation of Ser. No. 591,787, Oct. 2, 1990, abandoned.

[51] Int. Cl.[5] .................... G01N 27/04; G01N 35/02; G01N 7/00
[52] U.S. Cl. .......................... 422/90; 422/80; 422/81; 422/98; 436/51; 436/163; 436/181; 73/19.01; 73/19.1; 73/1 G
[58] Field of Search .............. 73/19.01, 19.1, 1 G; 422/83, 80, 81, 87, 90, 76, 78, 98; 436/51, 52, 163, 181

[56] References Cited

U.S. PATENT DOCUMENTS

| | | | |
|---|---|---|---|
| 4,288,229 | 9/1981 | Mar | 422/79 |
| 4,344,918 | 8/1982 | Takahashi | 422/78 |
| 4,526,755 | 7/1985 | Vincent et al. | 422/90 |
| 4,865,992 | 9/1989 | Hach et al. | 422/76 |
| 5,004,696 | 4/1991 | Clinkenbeard | 422/63 |

FOREIGN PATENT DOCUMENTS 2076459 4/1987 Japan ..................... 422/80

OTHER PUBLICATIONS

Coulometric total carbon dioxide for analysis for marine studies: Automation and calibration, pp. 117–132, 1987, Marine Chemistry.
Coulometric $TCO_2$ analysis for marine studies; An introduction, pp. 61–82, 1985, Marine Chemistry.

*Primary Examiner*—Robert J. Warden
*Assistant Examiner*—Christopher Y. Kim
*Attorney, Agent, or Firm*—Samuels, Gauthier & Stevens

[57] ABSTRACT

A system for coulometric $TCO_2$ analysis wherein a sample bottle is pressurized by a head space gas having a $CO_2$ composition which approximates the dissolved $CO_2$ concentration in the sample. The head space gas transfers to sample to a pipette. The sample is then transferred to a stripper where the sample is degassed. Two carrier gas lines flush the stripper and transfer the $CO_2$ to a coulometer.

7 Claims, 4 Drawing Sheets

METHOD AND APPARATUS FOR THE COULOMETRIC DETECTION OF DISSOLVED GASES PARTICULARLY $TCO_2$ IN SEAWATER

This is a continuation of application Ser. No. 07/591,787 filed on Oct. 2, 1990, abandoned.

BACKGROUND AND BRIEF SUMMARY OF THE INVENTION

The invention relates to a system and an automated method for the coulometric detection of dissolved gases. The method was developed for $CO_2$ using the theoretically most accurate method of detection, i.e., coulometry, but other detection schemes can be used. It is believed the most relevant prior art is set forth in the publications, Coulometric Total Carbon Dioxide Analysis for Marine Studies: Automation and Calibration: Marine Chemistry, 21 (1987) 117–133; and Coulometric $TCO_2$ Analysis for Marine Studies; An Introduction Marine Chemistry 16 (1985) 61–82, both of which references are incorporated by reference into this disclosure in their entireties.

Briefly, in the prior art system, there were three gas streams, a pneumatic gas stream, a carrier gas stream and a calibration gas stream. A sample bottle was placed in a thermostated bath. A pneumatic gas pressurized the sample bottle which caused the sample fluid to fill a glass pipette. Excess fluid from the filled pipette flowed into a vessel which contained a pair of sensing electrodes, which when covered with sea water completed an electrical circuit signalling the pipette was full. The pipette was then pressurized with the pneumatic gas. The sample drained from the pipette and flowed into a stripper where it was acidified and degassed to form an analyte, namely $CO_2$. A carrier gas carried the analyte to a coulometer where the $CO_2$ was measured. Pure $CO_2$ (99.995%) gas was used for system calibration.

In the inventive system disclosed herein, the volume of the seawater output from a water jacketed pipette to the stripper is determined gravimetrically. The sample bottle and the pipette are maintained at the same temperature. The sample stripper accommodates an auxiliary carrier gas flow in addition to the main flow. The auxiliary flow enters the stripper at the top and the main gas flow enters the stripper through the bottom. This ensures the quantitative recovery of analyte gases stripped from solution.

Further, in this system, a fourth gas stream called the head-space gas is used to pressurize the sample bottle and fill the pipette. The head space gas feature controls the gas composition of the head-space which develops in the sample bottle as the sample flows from the bottle into the pipette. For example, if the $TCO_2$ content of surface seawater is measured, compressed air (330 ppm $CO_2$) could be used as the head-space gas because surface seawater would already by equilibrated with air (atmosphere) containing 330 ppm $CO_2$. After the pipette is full, the sample bottle headspace is opened to the atmosphere to equalize the pressure inside and outside the bottle. At this point, the pressure and composition of the head-space gas inside the bottle are 1 atmosphere and 330 ppm $CO_2$, respectively. For a surface seawater equilibrated with the atmosphere as in the example above, the concentration of $CO_2$ is equal in both the water and air (330 ppm) at one atmosphere of pressure, and by using a head-space gas of compressed air this relationship is maintained during the analysis so that no $CO_2$ gas is likely to be forced into or out of the sample during the analysis in response to a concentration or pressure gradient. Note that only a small fraction of the $TCO_2$ in seawater is in the molecular phase as $CO_2$ gas, rather 99% appears in the ionic phase as bicarbonate or carbonate ions, but the coulometric titration is so sensitive that the small exchanges of molecular $CO_2$ into or out of the head-space could be measured, and cause under or over estimates of the true $TCO_2$ concentration. For seawater collected at depths $\geq 300$ meters, a head-space gas enriched in $CO_2$ (1000 ppm) would be used, but it is not necessary to custom fit the head-space gas to each sample because the exchange rate is slow compared to the analysis time and so much is known about the saturation status of seawater with respect to $CO_2$. However, in practice and principle an independent $CO_2$ containing head-space gas is demonstrably superior to the $CO_2$-free pneumatic gas used in the prior art. The above would also apply to other gases dissolved in seawater such as methane, hydrogen sulfide, etc. After the analysis is completed, the sample bottle is re-pressurized and the pipette re-filled and the cycle repeated for the next replicate.

A constrictor is placed in the line between the stripper and coulometer to create backpressure. Opening a solenoid valve causes the sample to immediately drain from the stripper. There is no possibility of a malfunction as happens from time to time with check valves because of spring failure, clogging, oxidation, condensation, etc. A second function of the restrictor is to prevent the coulometer cell solution from backing up into the input lines when momentary pressure differentials arise during operation.

BRIEF DESCRIPTION OF THE DRAWING(S)

DESCRIPTION OF THE PREFERRED EMBODIMENT(S)

The System

Figure 1:
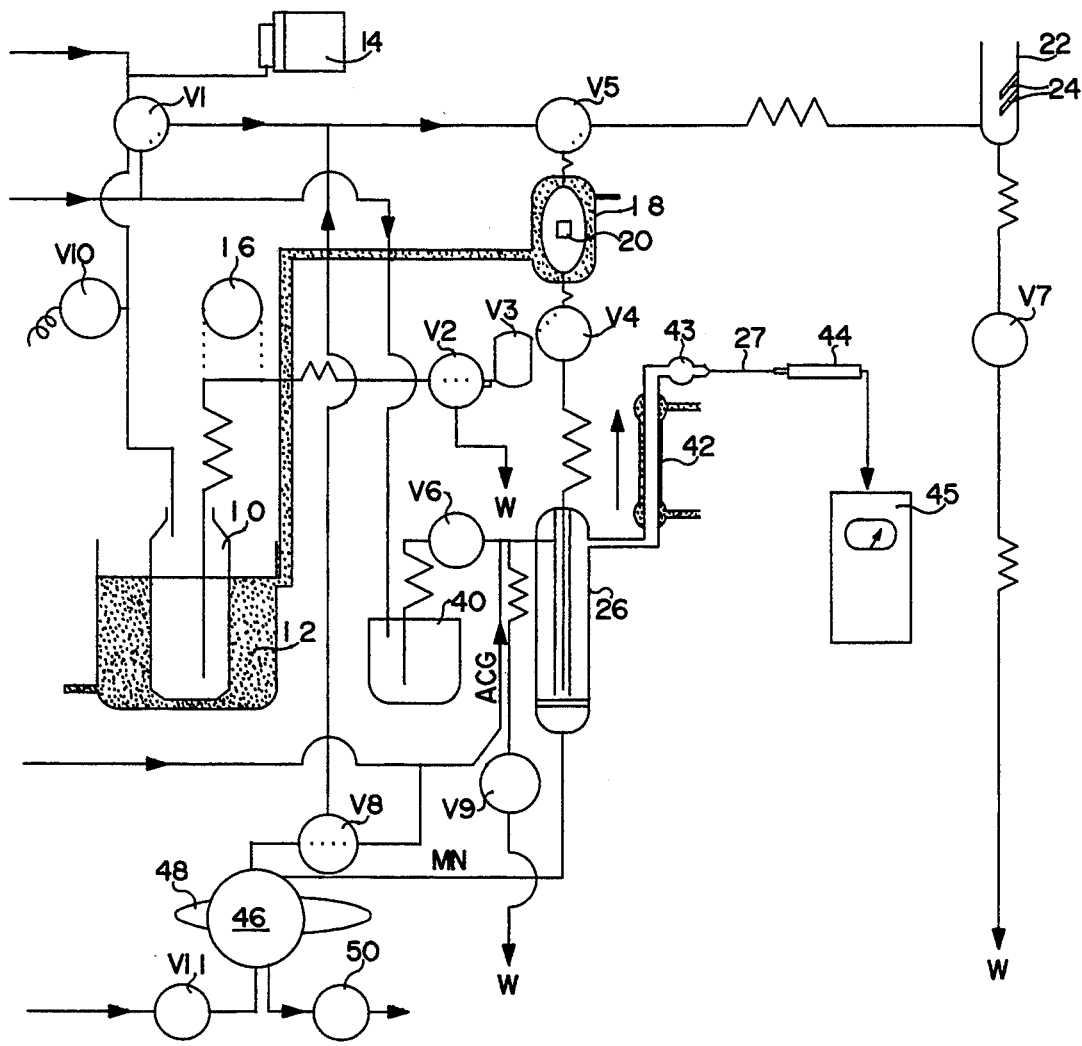
FIG. 1 is a process flow diagram of a system embodying the invention.

A system embodying the invention is shown in FIG. 1. Each of the components is a standard off-the-shelf item except for the stripper and pipette, which are custom made to accommodate an auxiliary carrier gas line and a water jacket, respectively, as will be described. The system comprises a sample bottle 10 in a thermostated bath 12. Either a pump 14, such as a diaphragm pump or a gas cylinder (not shown), provide a head-space gas mixture of known composition to pressurize the sample bottle 10 via a valve V1. This will cause the sample fluid to flow initially through valve V2 to waste to rinse the sample lines of the previous sample. Optionally provided is a parastolic pump 16 which can be used to move samples if desired. A water-jacketed pipette 18 includes a temperature sensor 20 which is read by a computer (not shown). The water in the bath 12 is in fluid flow communication with the water in the jacket of the pipette 18. A reservoir 22 communicates with the pipette 18. The reservoir 22 contains a pair of sensing electrodes 24.

Figure 2:
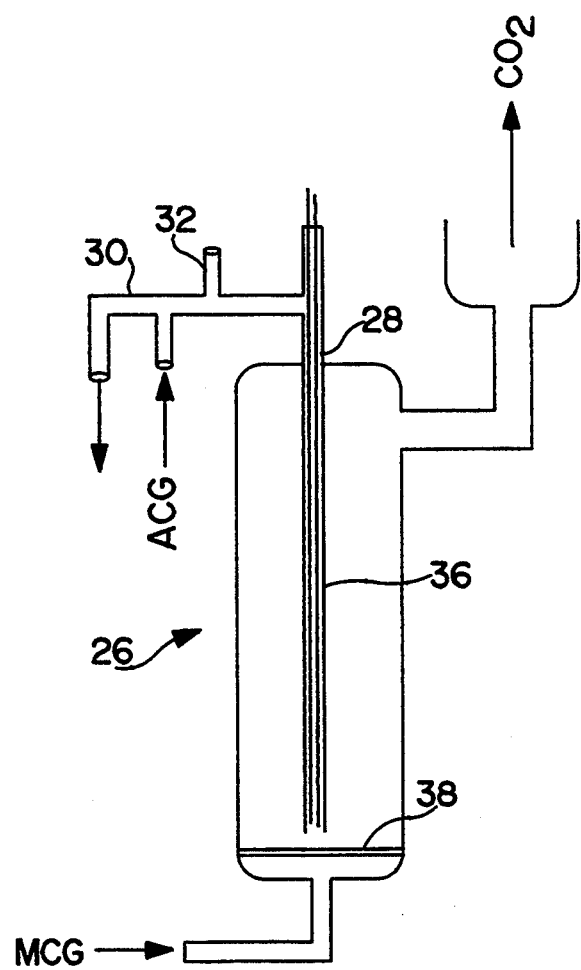
FIG. 2 is a schematic of a stripper used in the system.

A stripper 26 is in fluid flow communication with the pipette 18. Referring to FIG. 2, the stripper 26 is shown in greater detail and includes the main carrier gas line (MCG) and the auxiliary carrier gas line (ACG). Received in the column of the stripper is a central inlet tube 28 which includes an arm 30. The arm includes three lines, the ACG line just described, an acid line 32 and a drain line 34. Received within the central inlet tube is a sample inlet tube 36. Where the sample inlet tube, which carries the sample from the pipette into the stripper, enters the central inlet tube it is secured in a fluid-tight manner. The depending ends of the central inlet tube and the sample inlet tube are open and spaced apart from the bottom of the stripper just above a plate of course frit 38. The outer surface of the sample inlet tube 36 and the inner surface of the central inlet tube 28 define an annular ring-like passage through which the auxiliary carrier gas and acid flow in different steps of the process.

Referring to FIG. 1, communicating with the stripper 26 is a vessel of acid 40. A condenser 42, a water vapor trap 43, a constrictor 27, an acid vapor trap 44 and a coulometer 45 are downstream of the stripper. A gas sampling valve 46, communicating with the stripper 26, is provided with two sample loops 48 and 50.

Figure 3:
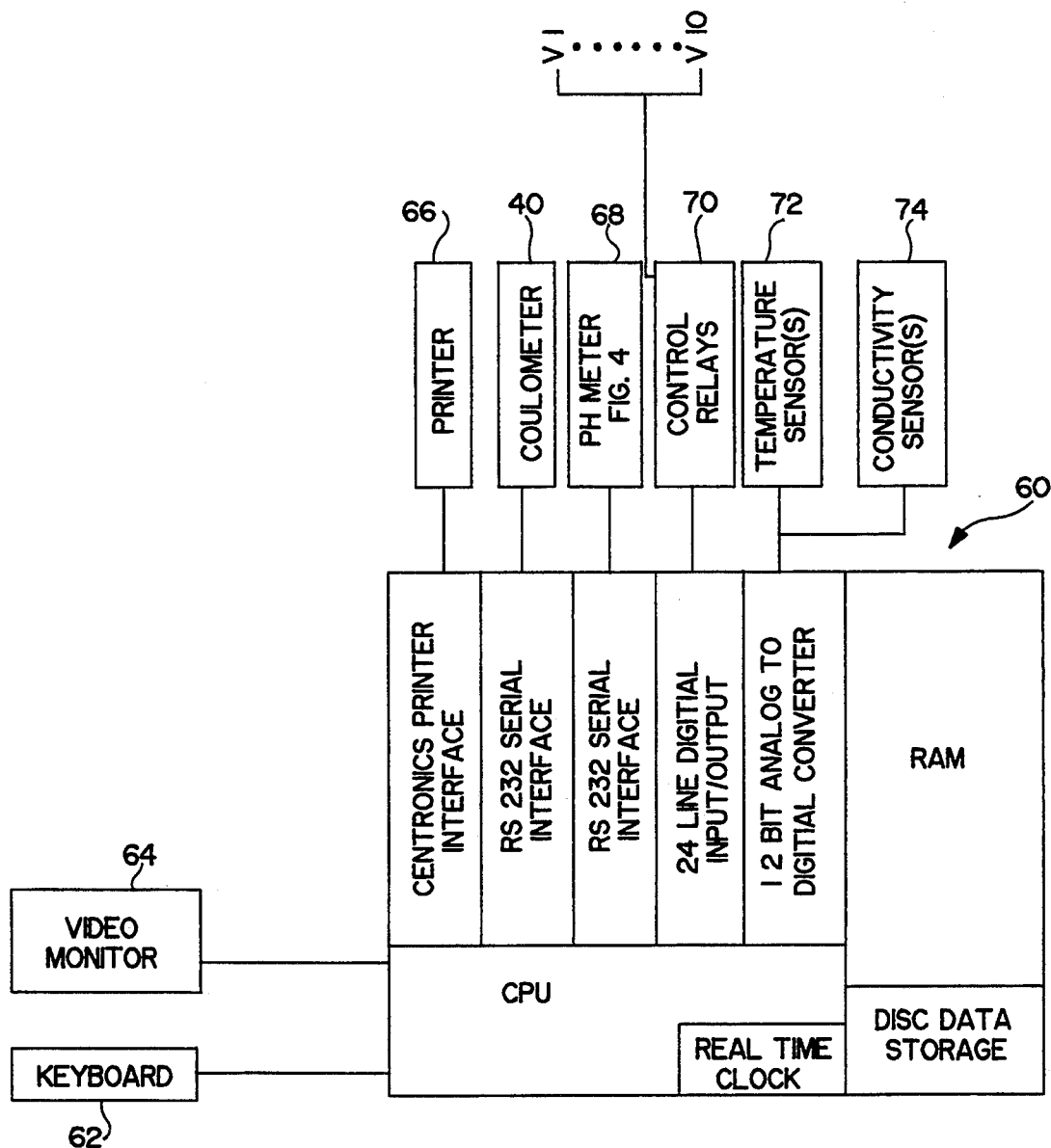
FIG. 3 is a functional block diagram of the system of FIG. 1.

Referring to FIG. 3, a computer, such as any IBM compatible, is shown generally at 60 and includes a keyboard 62 and a video monitor 64. A printer 66, the coulometer 40, a pH meter 68, control relays for the valves 70, temperature sensors 72 and conductivity sensors (electrodes) 74 are all interfaced to the computer 60. It is well known to those skilled in the art that the computer comprises the suitable interfaces, storage and computation units for performing arithmetical and logical functions on data processed in digital form. Any standard computer language consistent with the capability of a computer can be used with the instructions. The routines to effect the sequence of operations described in the following section, Operation, are not described in detail because they can be written in any desired notations, formats or sequence depending upon the particular computer being utilized, computer language, etc. The manufacturers handbook sets forth the necessary programs which include the sequence of internal interconnections which have been added by preparation and loading of the programs into the internal memory of the computer. Thus, the computer has loaded in the necessary programs to accomplish the following steps in the operation of the invention.

Operation

The operation of the system of the invention will be described with reference to the following non-limiting example. Unless otherwise noted, the control of temperatures, the sequence and duration of steps, the reading of data, and the operation of pumps, valves and the like is controlled by CPU. Also, unless otherwise indicated, the lines for the head space gas, pneumatic gas, carrier gas and calibration gas are pressurized.

Referring to FIG. 1, the bottle 10 is placed in the thermostated bath 12 where the temperature is maintained at between 1° to 2° C. below the in-situ temperature of the sample or alteratively at 10 ° C. The bottle stopper (not shown) is secured. A sample ID is input into the CPU via the keyboard. A head space gas, whose composition is between 330 and 1000 ppm $CO_2$ in $N_2$, is input into the bottle 10 by the pump 14 or gas cylinder through valve V1. Unless otherwise indicated, the valves V are three-way valves. A liquid sample having a composition of seawater and in an amount of ca. 10 ml initially flows through valve V2 to waste, W. While valve V3 (two way) is closed. This initial flow rinses the sample lines of previous sample. After rinsing, valve V2 is switched and valve V3 opened to allow the sample to flow through valves V4 and V5 and fill the water-jacketed pipette 18, which is maintained at the same temperature as the sample bath 12. The pressure of the head space gas is about 8 psig. The computer reads the temperature of the sample in the pipette. The excess liquid sample from the filled pipette 18 flows into the reservoir 22. The sensing electrodes 24, when covered with sea water, complete an electrical circuit which is measured by the computer. When the circuit is completed, the computer knows the pipette 18 is full; i.e. 25-30 ml (each pipette has a different volume). When the pipette is full, V10 is opened for four seconds to equalize the headspace pressure inside the bottle with atmospheric pressure.

Subsequently, valves V1, V4 and V5 are switched and V3 closed to allow $CO_2$-free pneumatic gas to flow through valves V1 and V5 resulting in the pipette being pressurized with a $CO_2$-free pneumatic gas at about 10 psig. Then, valve V4 is switched whereby the sample quickly drains from the pipette 18 through the valve V4 and through a 1/16 O.D. hydrophobic Teflon tube into the stripper where it is acidified and degassed. During this step, valves V3, V6, V8 and V9 are closed. This step constitutes a high-precision, pressure-mediated "to deliver" pipette. The precision of this to deliver pipette is better than 0.02% (at 25° C.). The sample volume going to the stripper 26 from the pipette 18 is determined gravimetrically by calibrating the specific pipette being used prior to its actual use.

Then, valve V4 closes and V8 opens. Carrier gas flows through the stripper to remove the analyte. The stripper 26 contains approximately 2 ml of 8.5% phosphoric acid ($H_3PO_4$).

To ensure that the gas-stripping is quantitative, the stripper 22 is supplied with two sources of carrier gas. This carrier gas can be the same composition as the pneumatic gas but both must be $CO_2$ free. The main source of carrier gas into the bottom of the stripper comes through valve V8, which is switched open, via the four-way valve 46 through the line marked MN. The auxiliary carrier gas enters the stripper from the top, valves V4, V5 and V6 being switched closed. This auxiliary carrier gas prevents the $CO_2$ from being sequestered in the central inlet tube of the stripper. The latter minimizes the stripper dead volume and the 1/16" O.D. lines used to feed the sample pipette minimizes system dead volume.

The gas stripped from the sample flows through a condenser, dehydrite and silica gel, all represented schematically from 42–44, and into the coulometer 45 where the titration is effected.

Coulometric titration per se is well known in the art and need not be described in detail. Briefly, in coulometry, the electricity required to convert all of a chemical species to a different chemical state is measured. The amount converted, in moles, is related to the quantity of electricity by Faraday's constant (96 489± two coulombs $mol^{-1}$). The coulometric titration of $CO_2$ involves the electrolytic generation of a strong base to titrate the weak acid formed by the reaction of the $CO_2$ and ethanolamine. Thus, $CO_2$ extracted from sea water is quantitatively converted to hydroxyethylcarbamic acid and titrated with OH− ions electrogenerated by the reduction of H₂O at a platinum cathode. The equivalence point is detected photometrically with thymolphthalein as indicator, and the complete sequence includes neutralization, redox and complexation reactions.

When the computer senses the end point of the titration, valve V9 is opened and the stripper is automatically drained due to the backpressure caused by the 1/16″ O.D. constrictor 27 downstream of the stripper.

After the stripper is emptied, valve V6 is switched open and acid, specifically 2 ml of 8.5% of $H_3PO_4$, from vessel 40 under pressure from the pneumatic gas is added to the stripper. Simultaneously, valve V7 is opened and the reservoir 22 is emptied under gravity. The valve sequence is set forth below.

Absorbant traps 70, such as charcoal or tenax, can be coupled to a gas chromatograph 72 for the analysis of hydrocarbons and EPA priority pollutants.

The temperature of water-jacketed pipette 18 is sensed through an AD 500 board to +0.1° C. This board measures the conductivity in the reservoir 22. A flow-through, free diffusion junction pH cell 74 communicates with the reservoir 22. It has a very rapid response (less than 30 seconds) and is stable to +0.002 pH units. Thus, the sample alkalinity and the partial pressure of the $CO_2$ ($pCO_2$) can be calculated from the pH cell and the coulometer 45. In addition to calculated alkalinity, a real time alkalinity titration can be incorporated into the system. Configured with proper filters, a $14_C$ count could also be done simultaneously with $TCO_2$ analysis.

| Step | Valve Sequence During Operation | | | | | | | | | |
|---|---|---|---|---|---|---|---|---|---|---|
| | V1 | V2 | V3 | V4 | V5 | V6 | V7 | V8 | V9 | V10 |
| Flush Lines | Open to HSC | Open to W | Closed | Closed | Closed | Closed | Closed | Closed | Closed | Closed |
| Filling Pipette | Open to HSC | Open to 18 | Open to 18 | Open to 18 | Open to 22 | Closed | Closed | Closed | Closed | Closed |
| Filled Pipette | Closed to HSC | Closed | Closed | Closed | Open to PG | Closed | Closed | Closed | Closed | Open |
| Filling Stripper | Open to PG | Closed | Closed | Open to 26 | Open to PG | Closed | Closed | Closed | Closed | Closed |
| Filled Stripper | Closed | Closed | Closed | Closed | Closed | Closed | Closed | Closed | Closed | Closed |
| During Titration | Closed | Closed | Closed | Closed | Closed | Closed | Closed | Open to GG | Closed | Closed |
| After Titration | Closed | Closed | Closed | Closed | Closed | Open | Open | Open to GG | Open | Closed |

Calibration

The calibration procedure, to ensure that the coulometer is performing to theory, consists of the gas sampling valve 46 connected to a pure source of $CO_2$ through an isolation valve V11. Opening the valve V11 fills either a sample loop 48 or 50. When the loop is filled, valve V8 is opened, the valve 46 is switched so that the carrier gas can flush the loop and carry the $CO_2$ through the stripper, the dryers and then to the coulometer in the same flow pattern, the carrier gas followed when carrying the analyte. The calibration procedure checks the efficiency of the stripper and at the same time it confirms the accuracy of the coulometer. The instantaneous barometric pressure and the loop temperature are input to the computer and the software corrects the volume of the loop with the difference between the observed temperature and the calibration temperature (25° C.) and then calculates from the gas law the mass of $CO_2$ in the loop. The calculated value is compared to the result obtained from the coulometric titration and if they agree the system is ready to analyze samples. The volumes of the loops are selected such that one full loop of pure $CO_2$ they will contain as much $CO_2$ as the water samples and expected to hold. For example, a 1.5 ml loop contains at one atmosphere approximately the same amount of $CO_2$ as 25 ml of acidified sea water (35 ppt). The loops 48 and 50 are immersed in a block of foam (not shown) for thermal stability.

Figure 4:
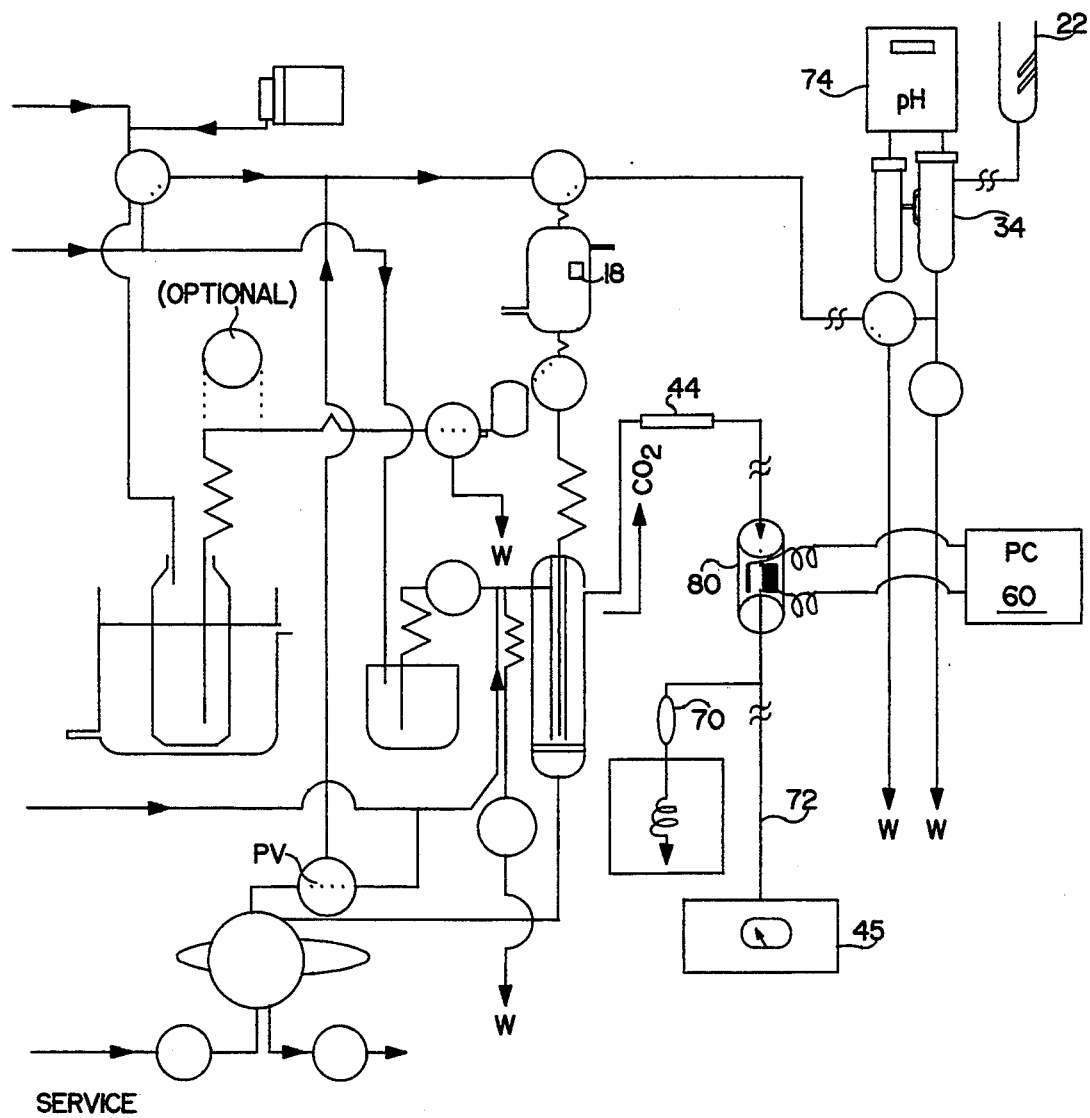
FIG. 4 is a process flow diagram of an alternative embodiment of the invention.

Alternative Embodiments

Where it is desired to measure dissolved oxygen based on reversed coulometry, referring to FIG. 4, a galvanic Hersh Cell (silver-lead electrode) can be interposed between the dryer 44 and the coulometer 45.

Although described in reference to the measurement of $TCO_2$ other gases that could easily be measured with the instrumentation are $CH_4$, hydrocarbons, $H_2S$, oxides of $N_2$, etc.

The system is configured as a single operator processor encompassing the major aquatic metabolic analysis and replaces the myriad of delicate but relatively imprecise electrodes, meters, detectors, glassware, pipettes, colorimetric tests, Winkler bottles, etc. now used in aquatic science. For example, the system can be used in a sewage treatment plant simply by programming the instrument to tell an operator exactly how efficiently a treatment tank was respiring by simultaneously monitoring $O_2$ and $CO_2$ concentrations and calculating the respiratory quotient (RQ) over time. Further, it could serve as a portable Warburg apparatus for any process tank (treatment tanks, fermenters, industrial makeup waters, batch or continuous cultures, aqua culture systems, etc.)

That is, it could be used also in purely analytical laboratories, especially for the pH, $TCO_2$ and $pCO_2$ of well or ground waters.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention what we now claim is:

1. An automated system for the coulometric detection of a dissolved carbon dioxide gas which comprises:

a vessel to store a liquid sample containing a dissolved carbon dioxide gas to be analyzed;

a water jacketed pipette to hold liquid sample transferred from the vessel;

means to place a pressurized head-space gas in communication with the sample in the vessel to transfer the sample from the vessel to the pipette, the head-space gas having the same concentration of carbon dioxide in the head-space gas as is present in the liquid sample to be analyzed;

means to place a pressurized pneumatic gas in communication with the sample in the pipette to drive the sample to a stripper where the dissolved carbon dioxide gas is stripped from the sample;

means to introduce a carrier gas into the stripper to carry the stripped gas; and a detector downstream of the stripper and in fluid flow communication with the stripper whereby the carrier gas carries the stripped gas to the detector.

2. The system of claim 1 which includes:

means to vent the head-space gas to atmosphere subsequent to the transfer of the liquid sample from the vessel to the pipette.

3. The system of claim 1 wherein the means to introduce the carrier gas into the stripper comprises a main gas line and an auxiliary gas line, the auxiliary gas line flowing into the stripper at a location spaced apart from the main gas line to ensure complete removal of the stripped gas.

4. The system of claim 1 which includes:

a reservoir downstream of and in communication with the pipette, the reservoir including a pair of electrodes whereby when liquid sample overflows the pipette it flows into the reservoir and completes an electrical circuit signaling the pipette is full.

5. The system of claim 1 which includes:

means to maintain the sample in the vessel and the sample in the pipette at substantially the same temperature.

6. The system of claim 5 wherein the means to detect comprises a coulometer to detect carbon dioxide.

7. The system of claim 1 wherein means to detect comprises means to detect dissolved oxygen.

* * * * *